United States Patent [19]

Huckestein et al.

[11] Patent Number: 5,461,159
[45] Date of Patent: Oct. 24, 1995

[54] BINDING CHEMICAL IMPURITIES CONTAINED IN CRUDE N-VINYLPYRROLID-2-ONE

[75] Inventors: Brigitta Huckestein; Rainer Blankenburg, both of Ludwigshafen; Herbert Helfert, Frankenthal, all of Germany

[73] Assignee: BASF Aktiengesellschaft, Ludwigshafen, Germany

[21] Appl. No.: 387,569

[22] Filed: Feb. 13, 1995

[30] Foreign Application Priority Data

Feb. 18, 1994 [DE] Germany ............... 44 05 199.9

[51] Int. Cl.$^6$ .................................. C07D 207/26
[52] U.S. Cl. ........................... 548/555; 548/543
[58] Field of Search ............................ 548/555

[56] References Cited

U.S. PATENT DOCUMENTS

| | | | |
|---|---|---|---|
| 2,828,307 | 3/1958 | Soeterbroek et al. | 260/239.3 |
| 4,837,338 | 6/1989 | Krupay et al. | 548/555 |
| 5,039,817 | 8/1991 | Kroker et al. | 548/543 |

FOREIGN PATENT DOCUMENTS 3736603  5/1989  Germany.

OTHER PUBLICATIONS

Ulmanns Encyklopadie der . . . Band 23, Verlag Chemie (1983) S. 611.

Khimiko–farmatsevticheskii . . . vol. 14, No. 1, pp. 79–80, Jan. (1980).

Polymer, 1985, vol. 26, Jun., S.945 ff.

*Primary Examiner*—David B. Springer
*Attorney, Agent, or Firm*—Keil & Weinkauf

[57] ABSTRACT

Chemical impurities contained in N-vinylpyrrolid-2-one are bound by a process in which the anhydride of an organic carboxylic acid is added to the crude N-vinylpyrrolid-2-one.

3 Claims, No Drawings

BINDING CHEMICAL IMPURITIES CONTAINED IN CRUDE N-VINYLPYRROLID-2-ONE

The present invention relates to a process for binding chemical impurities contained in crude N-vinylpyrrolid-2-one (for the sake of simplicity, the terms vinylpyrrolidone (instead of N-vinylpyrrolid-2-one) and pyrrolidone (instead of pyrrolid-2-one) are used below). Homo- and copolymers which are used for a very wide range of purposes (for example as adhesives or binders, as dispersants for pigments, as gloss agents for floor polishes or as film formers in pharmaceutical and cosmetic compositions) are prepared from vinylpyrrolidone.

Vinylpyrrolidone is produced industrially on a large scale essentially exclusively by reacting pyrrolidone with acetylene. The vinylation reaction is carried out in the liquid phase in the presence of catalytic pyrrolidone potassium at superatmospheric pressure and elevated temperatures (cf. for example Ullmanns Encyclopädie der technischen Chemie, Vol. 23, Verlag Chemie, Weinheim (1983), page 611). With an apparatus of standard technical complexity (use of a distillation column having up to 15 theoretical plates), a crude vinylpyrrolidone which is composed of about 95% by weight of vinylpyrrolidone, less than 0.5% by weight of impurities differing from pyrrolidone, and pyrrolidone as the remaining amount is usually produced by distillation of the reaction mixture. The impurities differing from pyrrolidone prove to be particularly troublesome. Our own investigations, too, have shown that they are responsible for the fact that colored products are obtained when crude vinylpyrrolidone is used for the preparation of polymers containing polymerized vinylpyrrolidone, particularly when the polymerization is carried out in protic solvents, such as ethanol or water, the polymerization process is based on a high conversion of the vinylpyrrolidone and residual vinylpyrrolidone is eliminated by adding an acid or a peroxide at elevated temperatures.

The type of impurities differing from pyrrolidone and contained in crude vinylpyrrolidone is not known specifically but comprises essentially basic impurities whose main component consists of organic amines.

In contrast to pyrrolidone, the other impurities of the crude vinylpyrrolidone can be separated off only with the use of special measures.

DE-A 37 36 603 recommends binding the basic impurities contained in crude vinylpyrrolidone by treating the latter with an acidic ion exchanger.

Although the resulting vinylpyrrolidone generally gives polymerization products which are not colored, the procedure of DE-A 37 36 603 is unsatisfactory in that the ion exchangers can no longer be regenerated after repeated use. This is presumably due to the fact that bases have a stabilizing effect on vinylpyrrolidone, and the product treated by means of acidic ion exchangers has a greater tendency to polymerize, so that polymer formed during the treatment with the ion exchanger reduces the regenerability of the ion exchangers.

Khimiko-farmatsevticheskii Zhurnal 14 No. 1, January 1980, 79–80, discloses that crude vinylpyrrolidone can be treated with diisocyanates and vinylpyrrolidone can then be isolated in higher purity by distillation. Although this procedure gives vinylpyrrolidone of satisfactory quality, it is unsatisfactory in that it requires the presence of toxic diisocyanates, which makes the distillative separation step indispensible.

As a possible alternative, the abovementioned publication recommends adding high molecular weight polycarboxylic acids to crude vinylpyrrolidone and then likewise isolating vinylpyrrolidone in high purity by distillation. The disadvantages of this procedure are on the one hand the necessity of the distillative separation step and, on the other hand, the fact that high molecular weight polycarbxoylic acids are extremely hygroscopic, i.e. they usually contain small amounts of water which hydrolyze vinylpyrrolidone in an acidic medium, resulting in undesirable losses of vinylpyrrolidone. Khimiko-farmatsevticheskii Zhurnal 14 No. 1, January 1980, 79–80, advises against a corresponding use of low molecular weight acids.

Polymer 26, June 1985, 945 et seq. discloses the purification of crude vinylpyrrolidone by zone melting. However, the disadvantage of this procedure is that it is not very suitable for large-scale industrial production.

It is an object of the present invention to provide a novel process for binding chemical impurities contained in crude vinylpyrrolidone, which process does not have the disadvantages of the prior art processes.

We have found that this object is achieved by a process for binding chemical impurities contained in crude vinylpyrrolidone, wherein the anhydride of an organic carboxylic acid is added to the crude vinylpyrrolidone. A particular advantage of the novel process is that it does not necessarily require a subsequent distillative separation step, i.e. crude vinylpyrrolidone containing the anhydride of an organic carboxylic acid, which anhydride, in contrast to diisocyanates, is generally not toxic, gives, even when used directly, polymers which are not colored. Furthermore, anhydrides of organic carboxylic acids are usually obtainable in a simple manner in anhydrous form, so that the novel process generally entails no loss of vinylpyrrolidone due to hydrolysis.

If the envisaged polymers of vinylpyrrolidone are obtained not only in noncolored form but, owing to a special intended use, also in generally higher purity, the addition of anhydride of an organic carboxylic acid to crude vinylpyrrolidone is advantageously followed by a distillative separation stage, which, if required, may be followed by further conventional purification steps. Where a subsequent distillative separation step is envisaged, those anhydrides of organic carboxylic acids whose boiling point at atmospheric pressure (1 atm≡1013 mmHg), $T_N^S$, is above that of vinylpyrrolidone are added to the crude vinylpyrrolidone, said addition being advantageous with regard to application. The difference in the boiling points is preferably at least 20° C. Under these conditions, highly pure vinylpyrrolidone is usually obtained at the top of the distillation column while the impurities bound to the added anhydride generally accumulate in the bottom of the column. Vinylpyrrolidone has a $T_N^S$ of 215° C. Thus, such suitable high-boiling anhydrides of organic carboxylic acids are, for example, succinic anhydride ($T_N^S$: 261° C.), phthalic anhydride ($T_N^S$: 284.5° C.), pyromellitic dianhydride (melting point at atmospheric pressure: 286° C.) and benzoic anhydride ($T_N^S$: 360° C.). As a rule, these high-boiling anhydrides of organic carboxylic acids are substances which are solid at standard temperature and pressure but which, as a rule, are soluble in vinylpyrrolidone at 25° C. in the amount to be used. Finally, however, solid anhydrides of organic carboxylic acids, which anhydrides are sparingly soluble or insoluble in vinylpyrrolidone, are also suitable for the novel process if they are used only in sufficiently finely divided form. They make it possible to replace any subsequent distillation step by a simple filtration.

Examples of such filterable anhydrides of organic carboxylic acids are homo- and copolymers of anhydrides of unsaturated aliphatic carboxylic acids, for example crosslinked homo- and copolymers of maleic anhydride (an example is the crosslinked copolymer of maleic anhydride and vinyl methyl ether (molar ratio 1:1)).

If the addition of an anhydride of an organic carboxylic acid is accompanied by a subsequent distillative separation step, this is advantageously carried out under reduced pressure. Distillation is usually effected at ≦20 mmHg.

If no subsequent distillative separation step is envisaged, it is also possible, according to the invention, to use low-boiling anhydrides of organic carboxylic acids. Examples are acetic anhydride, propionic anhydride, n-butyric anhydride, n-valeric anhydride and stearic anhydride. The successful anhydride addition according to the invention does not necessarily require elevated temperatures and can therefore also be carried out at room temperature. The amount of anhydride to be added is usually a few % by weight, as a rule <5% by weight, based on the amount of crude vinylpyrrolidone (if the anhydride is polymerized in a polymer, the stated amount is based only on the polymerized amount of anhydride).

The success of the novel process is probably due to the fact that the relevant impurities are evidently reactive primary and/or secondary amines which are bound to the anhydride with formation of an antide bond. Since the formation of the amide bond is accompanied by the formation of a carboxyl group, a subsequent distillative separation step is advisable whenever a large amount of amine impurities is present. If, in these circumstances, no distillative separation is carried out, the carboxyl groups formed result in a certain loss of vinylpyrrolidone, for example due to hydrolysis, in subsequent polymerization in protic solvents, for example water. That the anhydrides to be added are not capable of directly binding tertiary amines is seen as an advantage of the novel process, since small amounts of teriary amines are usually added to the purified vinylpyrrolidone as stabilizers against premature polymerization. Examples of such stabilizers are triethylamine and N,N'-di-sec-butyl-p-phenylenediamine, as well as tri-n-butylamine, N,N-dimethylbenzylamine, N,N-dimethylaniline, N,N-diethylaniline, N-methylmorpholine and p-N,N-dimethylaminopyridine. The last-mentioned amines have a boiling point comparable with that of vinylpyrrolidone and are therefore particularly suitable as stabilizers during the distillation of vinylpyrrolidone and are advantageously added in the novel process when it comprises a subsequent distillation stage. Finally, it should be stated that the novel process comprises in particular the treatment of crude vinylpyrrolidone from which pyrrolidone has already been separated off in a manner known per se. It should furthermore be stated that, if it comprises a subsequent distillation stage, the novel process leads to vinylpyrrolidone of higher purity, which also results in polymers having less odor. Furthermore, it is noteworthy that the novel process is also suitable for binding or separating off amine impurities in crude N-vinylcaprolactam.

EXAMPLES AND COMPARATIVE EXAMPLES

Comparative Example 1

A mixture of 70% by weight of crude vinylpyrrolidone and 30% by weight of vinyl acetate were subjected to free radical polymerization in ethanol at 80° C. using 0.5% by weight (based on the monomers) of α,α'-azobisisobutyronitrile as polymerization initiator, until the vinylpyrrolidone conversion was above 99.9 mol. %. In order to eliminate residual monomers, 0.3% by weight (based on the monomers) of di-tert-butyl hydroperoxide was then added and the mixture was stirred for 10 hours at 130° C. A colored ethanolic polymer solution was obtained. The solids content was 20% by weight.

Comparative Example 2

The crude vinylpyrrolidone from Comparative Example 1 was polymerized in water at 80° C. using 0.3% by weight of α,α'-azobisisobutyronitrile as polymerization initiator to give a 20% strength by weight aqueous polymer solution. The polymer conversion was above 99.9% by weight. Residual monomer was eliminated by reducing the pH of the aqueous solution to 4 by adding formic acid, and then stirring for 2 hours at 95° C. A colored aqueous polymer solution was obtained.

Example 1

5 g of succinic anhydride were added to 1 kg of crude vinylpyrrolidone from Comparative Example 1, and the resulting solution was stirred for 1 hour at room temperature. Comparative Examples 1 and 2 were then repeated with this mixture, in the case of the aqueous polymerization medium the pH being brought to 7 at the beginning of the polymerization by adding NaOH. In both cases, non-colored polymer solutions were obtained.

Example 2

The procedure was as in Example 1, except that vinylpyrrolidone of higher purity was subsequently separated off at 2 mmHg over a 30 cm Vigreux column by distillation. The remaining bottom product of the distillation had a deep reddish brown color. Comparative Examples 1 and 2 were repeated with the vinylpyrrolidone separated off by distillation. In both cases, non-colored polymer solutions which had a reduced odor were obtained.

Example 3

The procedure was as in Example 2, except that, instead of succinic anhydride, the corresponding amount of phthalic anhydride was used. In this case, too, non-colored polymers having reduced odor were obtained.

Comparative Example 3

The distillation in Example 2 was repeated, but without the addition of succinic anhydride. Comparative Examples 1 and 2 were repeated with the vinylpyrrolidone separated off by distillation. In both cases, colored polymer solutions were obtained.

Comparative Example 4

The procedure was as in Example 1, except that, instead of succinic anhydride, an equivalent amount of phosphoric acid was added. Colored polymer solutions were obtained.

Comparative Example 5

The procedure was as in Example 2, except that, instead of succinic anhydride, an aquivalent amount of phosphoric acid was added. Colored polymer solutions were obtained.

We claim:
1. A process for binding chemical impurities contained in crude N-vinylpyrrolid-2-one, wherein an anhydride of an organic carboxylic acid is added to the crude N-vinylpyr- rolidone.

2. A process as claimed in claim 1, wherein an anhydride which is soluble in N-vinylpyrrolid-2-one and whose boiling point at atmospheric pressure (1 atm≡1013 mmHg) is above the boiling point of N-vinylpyrrolid-2-one is added and, after the addition of the anhydride, N-vinylpyrrolid-2-one is separated off from the resulting solution under reduced pressure by distillation.

3. A process as claimed in claim 1, wherein an anhydride which is insoluble in N-vinylpyrrolid-2-one is added in finely divided form and the insoluble fraction is then separated off from the resulting mixture by filtration.

* * * * *